US012788501B2

(12) United States Patent
Santos et al.

(10) Patent No.: US 12,788,501 B2
(45) Date of Patent: Nov. 10, 2026

(54) SYSTEM AND METHOD FOR GENERATING AN INITIAL TRANSFORMATION MATRIX USING POSITION DATA OF A TRACKED INSTRUMENT MOVED ALONG A PREDEFINED TRAJECTORY TO REGISTER IMAGING DATA

(71) Applicant: GE Precision Healthcare LLC, Waukesha, WI (US)

(72) Inventors: Alba Garcia Santos, Copenhagen (DK); Jacob Bjerring Olesen, Copenhagen (DK); Fredrik Gran, Limhamn (SE)

(73) Assignee: GE Precision Healthcare LLC, Waukesha, WI (US)

( * ) Notice: Subject to any disclaimer, the term of this patent is extended or adjusted under 35 U.S.C. 154(b) by 40 days.

(21) Appl. No.: 18/643,265

(22) Filed: Apr. 23, 2024

(65) Prior Publication Data

US 2025/0325328 A1 Oct. 23, 2025

(51) Int. Cl.
*A61B 34/20* (2016.01)
*G06T 7/37* (2017.01)

(52) U.S. Cl.
CPC ................ *A61B 34/20* (2016.02); *G06T 7/37* (2017.01); *A61B 2034/2065* (2016.02); (Continued)

(58) Field of Classification Search
CPC ... A61B 34/20; A61B 2034/2065; G06T 7/37; G06T 2207/10081; G06T 2207/10088; G06T 2207/30004; G06T 2207/30241
See application file for complete search history.

(56) References Cited

U.S. PATENT DOCUMENTS 8,781,186 B2 7/2014 Clements et al.
10,290,076 B2 5/2019 Kadoury et al.
(Continued)

FOREIGN PATENT DOCUMENTS

CN 106023140 A 10/2016
WO WO-2017017498 A1 * 2/2017 ........... A61B 5/0064
WO WO-2022229937 A1 * 11/2022 ............. A61B 1/307

OTHER PUBLICATIONS

Riddle et al. "Extracting data from a DICOM file." Medical physics 32.6Part1 (2005): 1537-1541 (Year: 2005).*
(Continued)

*Primary Examiner* — Anne M Kozak
*Assistant Examiner* — Jason P Gross
(74) *Attorney, Agent, or Firm* — SPQ IP LLC

(57) ABSTRACT

Various systems and methods are provided for generating an initial transformation matrix for registering intraoperative imaging data with preoperative imaging data. Position data of a tracked instrument that is moved in a trajectory corresponding to a predefined shape relative to a patient may be received. A first set of coordinates of the position data corresponding to the predefined shape may be determined. Preoperative imaging data of the patient may be received. A second set of coordinates of the preoperative imaging data corresponding to the predefined shape may be determined. The initial transformation matrix may be generated based on the first set of coordinates and the second set of coordinates. The intraoperative imaging data may be registered with the preoperative imaging data based on the initial transformation matrix.

11 Claims, 11 Drawing Sheets

(52) U.S. Cl.
CPC ............... *G06T 2207/10081* (2013.01); *G06T 2207/10088* (2013.01); *G06T 2207/30004* (2013.01); *G06T 2207/30241* (2013.01)

(56) References Cited

U.S. PATENT DOCUMENTS

| | | | | |
|---|---|---|---|---|
| 2008/0123927 | A1* | 5/2008 | Miga | A61B 90/36 382/131 |
| 2008/0205719 | A1* | 8/2008 | Pekar | G06T 7/33 382/128 |
| 2008/0255442 | A1 | 10/2008 | Ashby et al. | |
| 2011/0274324 | A1* | 11/2011 | Clements | A61B 90/36 382/128 |
| 2014/0193053 | A1* | 7/2014 | Kadoury | A61B 90/36 382/128 |
| 2015/0157416 | A1* | 6/2015 | Andersson | A61B 17/1757 606/102 |
| 2016/0157938 | A1* | 6/2016 | Breisacher | G16H 30/20 382/128 |
| 2017/0056057 | A1* | 3/2017 | Thapliyal | A61B 8/12 |
| 2018/0268541 | A1* | 9/2018 | Kruecker | G06F 3/017 |
| 2020/0268348 | A1* | 8/2020 | Park | G06T 7/0012 |
| 2020/0321099 | A1* | 10/2020 | Holladay | G16H 30/20 |
| 2022/0125517 | A1* | 4/2022 | Zimmermann | A61B 34/20 |
| 2024/0260945 | A1* | 8/2024 | Shahedi | A61B 34/20 |

OTHER PUBLICATIONS

Gueziri, Houssem-Eddine, and D. Louis Collins. "Fast registration of ct with intra-operative ultrasound images for spine surgery." International Workshop and Challenge on Computational Methods and Clinical Applications for Spine Imaging. Cham: Springer International Publishing, 2018. (Year: 2018).*

Audette, Michel A., Frank P. Ferrie, and Terry M. Peters. "An algorithmic overview of surface registration techniques for medical imaging." Medical image analysis 4.3 (2000): 201-217. (Year: 2000).*

Zou, Xuyan, et al. "Automatic 3D point cloud registration algorithm based on triangle similarity ratio consistency." IET Image Processing 14.14 (2020): 3314-3323. (Year: 2020).*

Wolfson, Haim J., and Isidore Rigoutsos. "Geometric hashing: An overview." IEEE computational science and engineering 4.4 (2002): 10-21. (Year: 2002).*

* cited by examiner

SYSTEM AND METHOD FOR GENERATING AN INITIAL TRANSFORMATION MATRIX USING POSITION DATA OF A TRACKED INSTRUMENT MOVED ALONG A PREDEFINED TRAJECTORY TO REGISTER IMAGING DATA

TECHNICAL FIELD

The present disclosure relates, generally, to a system and a method for generating an initial transformation matrix for registering intraoperative imaging data with preoperative imaging data.

BACKGROUND

The registration of intraoperative imaging data with preoperative imaging data has various applications. For instance, intraoperative imaging data acquired using a real-time imaging modality (e.g., ultrasound) may be registered with preoperative imaging data acquired using a high-resolution imaging modality (e.g., computed tomography (CT)) to enable a surgeon to navigate an interventional device to a region of interest of a patient during surgery, assist a surgeon in assessing the region of interest, or the like. In some cases, the registration of the intraoperative imaging data with the preoperative imaging data might require fiducials to be placed relative to the patient during the acquisition of both the intraoperative imaging data and the preoperative imaging data. This technique might prove to be time-consuming, error-prone, and/or impossible. In other cases, the registration of the intraoperative imaging data with the preoperative imaging data might require the matching of anatomical landmarks in the intraoperative imaging data and the preoperative imaging data. This technique might also prove to be time-consuming, computationally expensive, error-prone, etc.

SUMMARY

This summary introduces concepts that are described in more detail in the detailed description. It should not be used to identify essential features of the claimed subject matter, nor to limit the scope of the claimed subject matter.

In an aspect, a method may include receiving position data of a tracked instrument that is moved in a trajectory corresponding to a predefined shape relative to a patient; determining a first set of coordinates of the position data corresponding to the predefined shape; receiving preoperative imaging data of the patient; determining a second set of coordinates of the preoperative imaging data corresponding to the predefined shape; generating an initial transformation matrix based on the first set of coordinates and the second set of coordinates; and registering intraoperative imaging data with the preoperative imaging data based on the initial transformation matrix.

In another aspect, a device may include a memory configured to store instructions; and one or more processors configured to execute the instructions to perform operations comprising: receiving position data of a tracked instrument that is moved in a trajectory corresponding to a predefined shape relative to a patient; determining a first set of coordinates of the position data corresponding to the predefined shape; receiving preoperative imaging data of the patient; determining a second set of coordinates of the preoperative imaging data corresponding to the predefined shape; generating an initial transformation matrix based on the first set of coordinates and the second set of coordinates; and registering intraoperative imaging data with the preoperative imaging data based on the initial transformation matrix.

In yet another aspect, non-transitory computer-readable medium may store instructions that, when executed by one or more processors, cause the one or more processors to perform operations comprising: receiving position data of a tracked instrument that is moved in a trajectory corresponding to a predefined shape relative to a patient; determining a first set of coordinates of the position data corresponding to the predefined shape; receiving preoperative imaging data of the patient; determining a second set of coordinates of the preoperative imaging data corresponding to the predefined shape; generating an initial transformation matrix based on the first set of coordinates and the second set of coordinates; and registering intraoperative imaging data with the preoperative imaging data based on the initial transformation matrix.

DETAILED DESCRIPTION

As addressed above, techniques for registration of intraoperative imaging data and preoperative imaging data might prove time-consuming, error-prone, impossible, or the like. Further, these techniques might necessitate the usage of various fiducials, might require the performance of particular tasks by medical personnel, might require accurate alignment of the patient relative to the imaging equipment, or the like.

Some embodiments herein are directed to a technique for generating an initial transformation matrix for registering intraoperative imaging data with preoperative imaging data using position data of a tracked instrument that is moved in a trajectory corresponding to a predefined shape relative to a patient and metadata of the preoperative imaging data. In this way, some of the embodiments herein provide a fast, efficient, and easy technique for generating an initial transformation matrix. Further, in this way, some of the embodiments herein may improve the robustness of the final registration algorithm, which can improve the accuracy of registration of intraoperative imaging data with preoperative imaging data.

Figure 1:
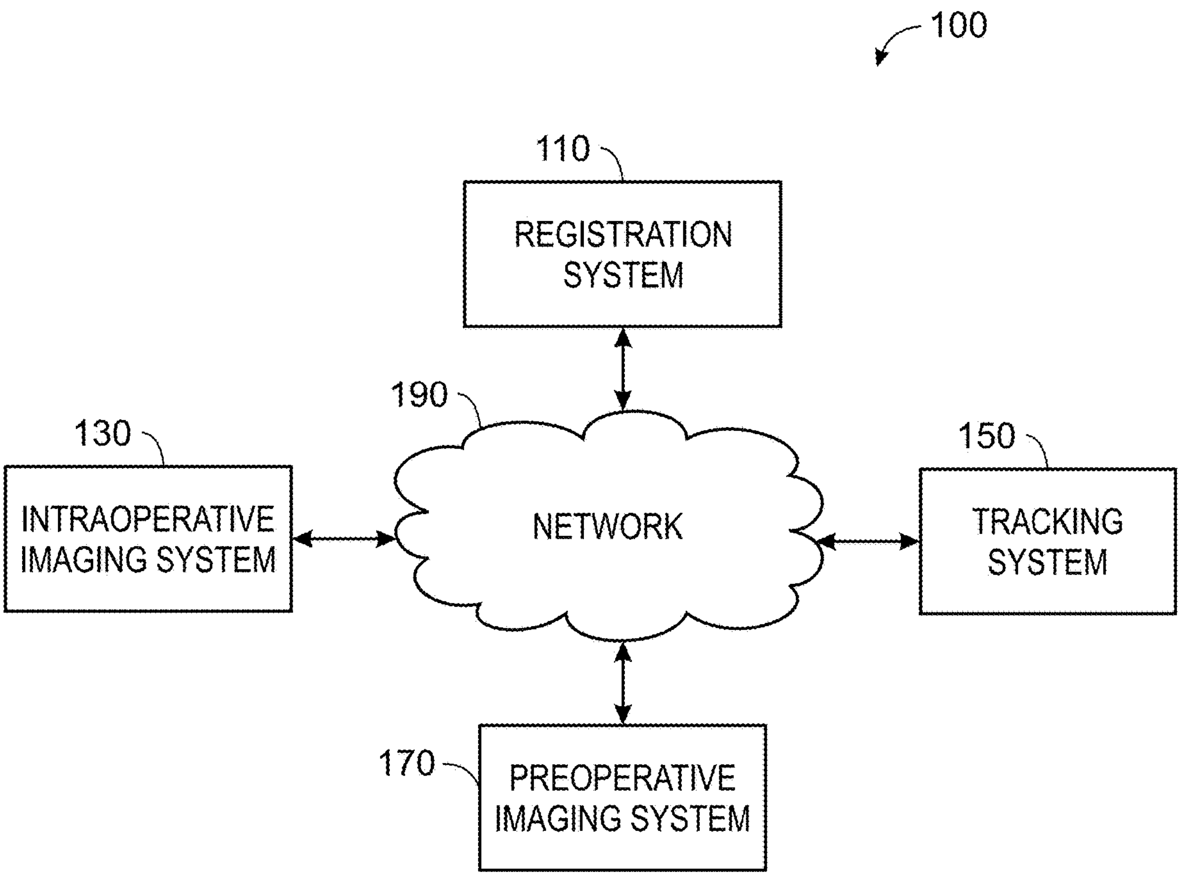
FIG. 1 is a diagram of an example system for generating an initial transformation matrix for registering intraoperative imaging data with preoperative imaging data based on position data of a tracked instrument that is moved in a trajectory corresponding to a predefined shape relative to a patient and metadata of the preoperative imaging data.

FIG. 1 is a diagram of an example system 100 for generating an initial transformation matrix for registering intraoperative imaging data with preoperative imaging data based on position data of a tracked instrument that is moved in a trajectory corresponding to a predefined shape relative to a patient and metadata of the preoperative imaging data. As shown in FIG. 1, the system 100 may include a registration system 110, an intraoperative imaging system 130, a tracking system 150, a preoperative imaging system 170, and a network 190.

The registration system 110 may be configured to generate an initial transformation matrix for registering intraoperative imaging data with preoperative imaging data based on position data of a tracked instrument that is moved in a trajectory corresponding to a predefined shape relative to a patient and metadata of the preoperative imaging data. For example, the registration system 110 may be a server, a workstation, a medical device, a computer, or the like.

The intraoperative imaging system 130 may be configured to acquire intraoperative imaging data of a region of interest of a patient. For example, the intraoperative imaging system 130 may be an ultrasound system, such as a 2D ultrasound system, a 3D ultrasound system, a 4D ultrasound system, a Doppler ultrasound system, or the like. Alternatively, the intraoperative imaging system may be a system of a different imaging modality than ultrasound, such as an optoacoustic imaging system, a photoacoustic imaging system, a thermoacoustic imaging system, or the like. The intraoperative imaging data may be acquired, generated, or the like, during the occurrence of a medical procedure involving a patient.

The tracking system 150 may be configured to acquire tracking data. For example, the tracking system 150 may be an electromagnetic tracking system, an optical tracking system, an acoustic tracking system, an inertial tracking system, or the like.

The preoperative imaging system 170 may be configured to acquire preoperative imaging data of the region of interest of the patient. For example, the preoperative imaging system 170 may be a CT system, a magnetic resonance imaging (MRI) system, an ultrasound system, an X-ray system, a positron emission tomography (PET) device, or the like. The preoperative imaging data may be acquired, generated, or the like, before the occurrence of a medical procedure involving a patient.

The network 190 may permit communication between the registration system 110, the intraoperative imaging system 130, the tracking system 150, and the preoperative imaging system 170. For example, the network 190 may be a local area network (LAN), a wide area network (WAN), a metropolitan area network (MAN), a cellular network, a private network, an ad hoc network, an intranet, the Internet, a fiber optic-based network, or the like, and/or a combination of these or other types of networks.

The number and arrangement of the systems of the system 100 are provided as an example. In practice, the system 100 may include additional systems, fewer systems, different systems, or differently arranged systems than those shown in FIG. 1. Additionally, or alternatively, a set of systems (e.g., one or more systems) of the system 100 may be integrated into a single system, and/or perform one or more functions described as being performed by another system, or set of systems, of the system 100.

Figure 2:
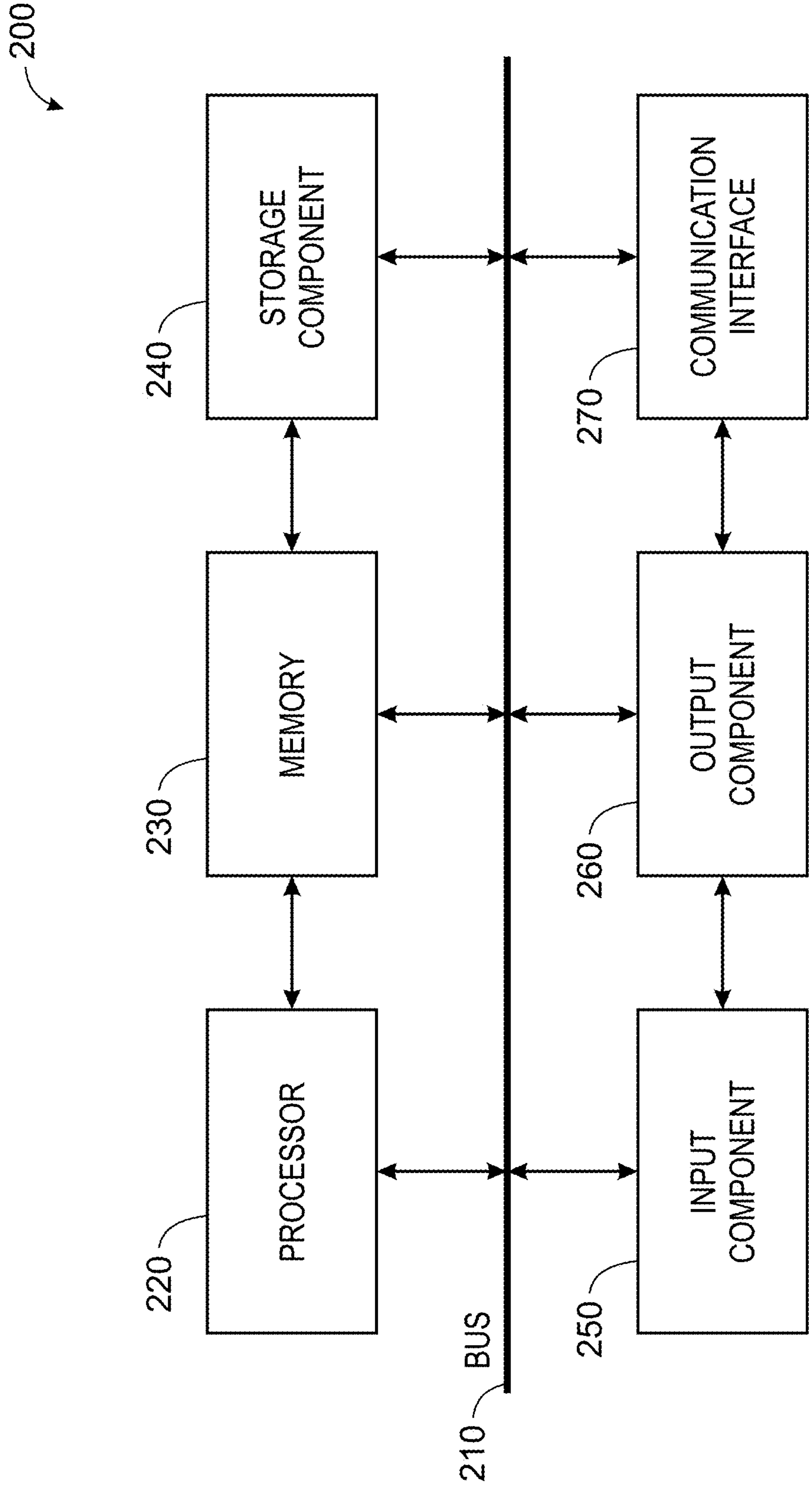
FIG. 2 is a diagram of example components of a system.

FIG. 2 is a diagram of example components of a system 200. The system 200 may correspond to the registration system 110, the intraoperative imaging system 130, the tracking system 150, and/or the preoperative imaging system 170. As shown in FIG. 2, the system 200 may include a bus 210, a processor 220, a memory 230, a storage component 240, an input component 250, an output component 260, and a communication interface 270.

The bus 210 includes a component that permits communication among the components of the system 200. The processor 220 may be implemented in hardware, firmware, or a combination of hardware and software. The processor 220 may be a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component.

The processor 220 may include one or more processors capable of being programmed to perform a function. The processor 220 may include one or more processors 220 configured to perform the operations described herein. For example, a single processor 220 may be configured to perform all of the operations described herein. Alternatively, multiple processors 220, collectively, may be configured to perform all of the operations described herein, and each of the multiple processors 220 may be configured to perform a subset of the operations descried herein. For example, a first processor 220 may perform a first subset of the operations described herein, a second processor 220 may be configured to perform a second subset of the operations described herein, etc.

The memory 230 may include a random access memory (RAM), a read only memory (ROM), and/or another type of dynamic or static storage device (e.g., a flash memory, a magnetic memory, and/or an optical memory) that stores information and/or instructions for use by the processor 220.

The storage component 240 may store information and/or software related to the operation and use of the system 200. For example, the storage component 240 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

The input component 250 may include a component that permits the system 200 to receive information, such as via user input (e.g., a touch screen display, a keyboard, a keypad, a mouse, a button, a switch, a camera, and/or a microphone). Additionally, or alternatively, the input component 250 may include a sensor for sensing information (e.g., a global positioning system (GPS) component, an accelerometer, a gyroscope, and/or an actuator). The output component 260 may include a component that provides output information from the system 200 (e.g., a display, a speaker for outputting sound at the output sound level, and/or one or more light-emitting diodes (LEDs)).

The communication interface 270 may include a transceiver-like component (e.g., a transceiver and/or a separate receiver and transmitter) that enables the system 200 to communicate with other systems, such as via a wired connection, a wireless connection, or a combination of wired and wireless connections. The communication interface 270 may permit the system 200 to receive information from another system and/or provide information to another system. For example, the communication interface 270 may include an Ethernet interface, an optical interface, a coaxial interface, an infrared interface, a radio frequency (RF) interface, a universal serial bus (USB) interface, a Wi-Fi interface, a cellular network interface, or the like.

The system 200 may perform one or more processes described herein. The system 200 may perform these processes based on the processor 220 executing software instructions stored by a non-transitory computer-readable medium, such as the memory 230 and/or the storage component 240. A computer-readable medium may be defined herein as a non-transitory memory device. A memory device may include memory space within a single physical storage device or memory space spread across multiple physical storage devices.

The software instructions may be read into the memory 230 and/or the storage component 240 from another computer-readable medium or from another system via the communication interface 270. When executed, the software instructions stored in the memory 230 and/or the storage component 240 may cause the processor 220 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of the components shown in FIG. 2 are provided as an example. In practice, the system 200 may include additional components, fewer components, different components, or differently arranged components than those shown in FIG. 2. Additionally, or alternatively, a set of components (e.g., one or more components) of the system 200 may perform one or more functions described as being performed by another set of components of the system 200.

Figure 3:
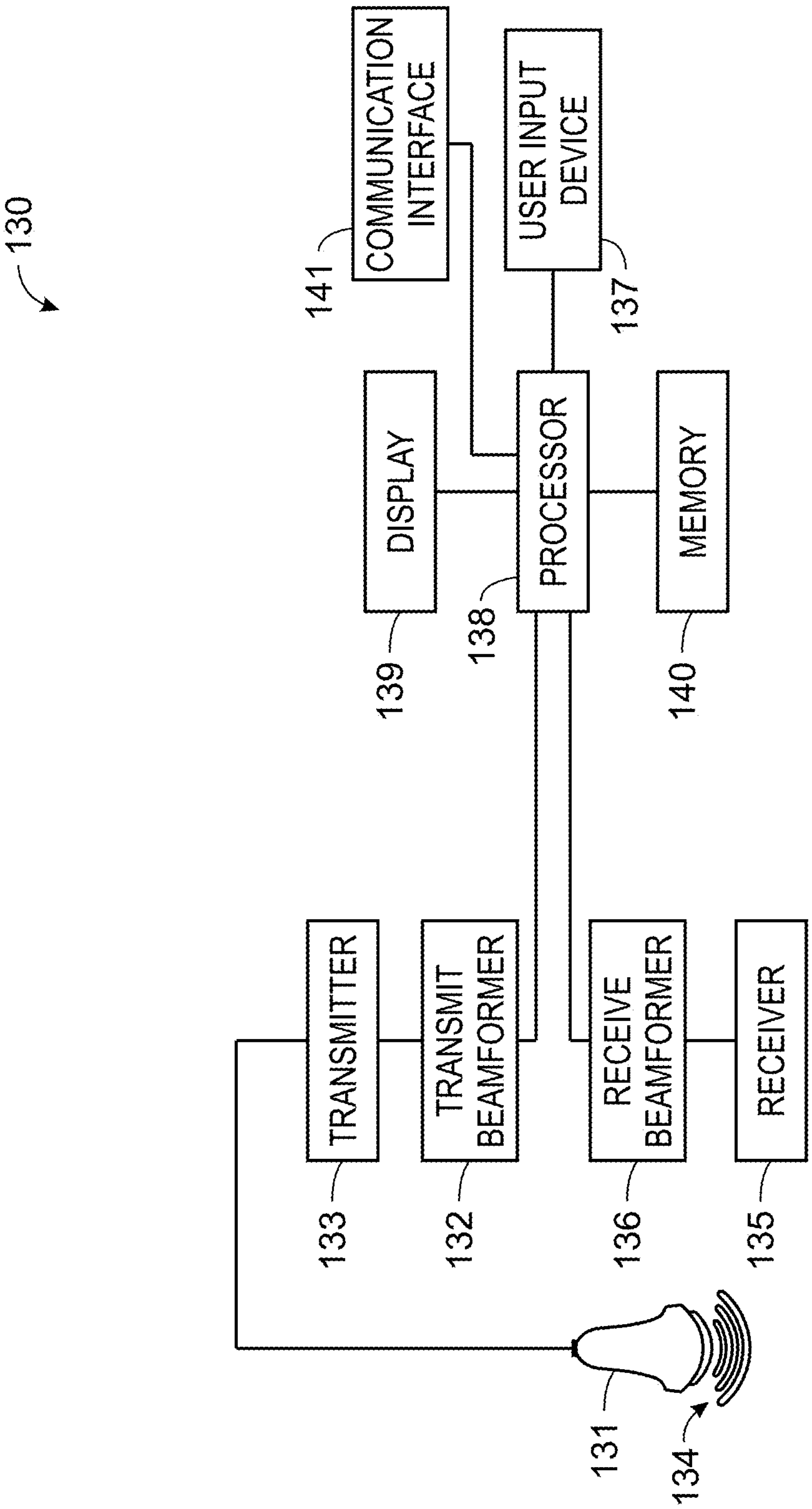
FIG. 3 is a diagram of example devices of an ultrasound system of FIG. 1.

FIG. 3 is a diagram of example devices of an intraoperative imaging system 130 of FIG. 1. As shown in FIG. 3, the intraoperative imaging system 130 may be an ultrasound system, and may include an ultrasound probe 131, a transmit beamformer 132, a transmitter 133, elements 134, a receiver 135, a receive beamformer 136, a user input device 137, a processor 138, a display 139, a memory 140, and a communication interface 141. The foregoing components may be connected via wired or wireless connections.

The ultrasound probe 131 may be configured to acquire ultrasound data. For example, the ultrasound probe 131 may be a linear probe, a phase array probe, a curved linear probe coupled with a position tracking system, a mechanically steered linear array transducer, a phased array transducer, a curved linear array transducer, an electronically steered 2D transducer array, an electronic 3D (e3D) probe, an electronic 4d (e4D) probe, a low profile wearable patch version of any of the foregoing probes, or the like. According to an embodiment, the ultrasound probe 131 may be configured to generate ultrasound signals, emit the ultrasound signals towards a region of interest of a subject, receive echo ultrasound signals that are back-scattered from the region of interest of the subject, generate ultrasound data based on the echo ultrasound signals, and output the ultrasound data. The region of interest may be any region of the anatomy of a subject. The subject may be a person, an animal, a phantom, or the like.

The transmit beamformer 132 may be configured to apply delay times to electrical signals provided to the elements 134 to focus corresponding ultrasound signals at the region of interest. The transmitter 133 may be configured to transmit electrical signals to the elements 134 to drive the elements 134 to emit ultrasound signals towards the region of interest. The elements 134 may be configured to receive the electrical signals from the transmitter 133, convert the electrical signals into ultrasound signals, and emit the ultrasound signals towards the region of interest. The elements 134 may be configured to receive echo ultrasound signals that are back-scattered by the region of interest, convert the echo ultrasound signals into electrical signals, and provide the electrical signals to the receiver 135. The receiver 135 may be configured to receive electrical signals from the elements 134, and provide the electrical signals to the receive beamformer 136. The receive beamformer 136 may apply delay times to the electrical signals received from the elements 134.

The user input device 137 may be configured to receive a user input, and provide the user input to the processor 138. For example, the user input device 137 may be a touch screen display, a keyboard, a keypad, a mouse, a button, a switch, a microphone, or the like. Additionally, or alternatively, the user input device 137 may be configured to sense information. For example, the user input device 137 may sense information from an electro-magnetic positioning system, an inertial measurement system, an accelerometer, a gyroscope, an actuator, or the like.

The processor 138 may be configured to perform the operations as described herein. For example, the processor 138 may be a CPU, a GPU, an APU, a microprocessor, a microcontroller, a DSP, an FPGA, an ASIC, or the like. The processor 138 may be implemented in hardware, firmware, or a combination of hardware and software. The processor 138 may include one or more processors 138 configured to perform the operations described herein. For example, a single processor 138 may be configured to perform all of the operations described herein. Alternatively, multiple processors 138, collectively, may be configured to perform all of the operations described herein, and each of the multiple processors 138 may be configured to perform a subset of the operations descried herein. For example, a first processor 138 may perform a first subset of the operations described herein, a second processor 138 may be configured to perform a second subset of the operations described herein, etc.

The processor 138 may be configured to control the ultrasound probe 131 to acquire ultrasound data. The processor 138 may be configured to control which of the elements 134 are active, and control the shape of a beam emitted from the ultrasound probe 131. The processor 138 may generate ultrasound images for display. For example, the processor 138 may generate B-mode images, color Doppler images, M-mode images, color M-mode images, or the like. The ultrasound images may be 3D images, 2D images, single plane images, bi-plane images, three-plane images, multi-plane images, or the like. The ultrasound images may correspond to various anatomical planes (e.g., sagittal, coronal, and transverse) of the region of interest.

The display 139 may be configured to display information. For example, the display 139 may be a monitor, an LED display, a cathode ray tube, a projector display, a touchscreen, tablet computer, mobile phone, or the like. The display 139 may display ultrasound images based on the ultrasound data in real-time. For example, the display 139 may display the ultrasound images within one second, two seconds, five seconds, etc., of the ultrasound data being acquired by the ultrasound probe 131.

The memory 140 may be configured to store information and/or instructions for use by the processor 138. The memory 140 may be a non-transitory computer-readable medium. For example, the memory 140 may be a RAM, a ROM, a flash memory, a magnetic memory, an optical memory, or the like. The memory 140 may be configured to store instructions that, when executed by the processor 138, cause the processor 138 to perform the operations described herein.

The communication interface 141 may be configured to enable the processor 138 to communicate with other systems, such as via a wired connection, a wireless connection, or a combination of wired and wireless connections. For example, the communication interface 141 may include an Ethernet interface, an optical interface, a coaxial interface, an infrared interface, an RF interface, a USB interface, a Wi-Fi interface, a cellular network interface, or the like.

The number and arrangement of the components of the intraoperative imaging system 130 shown in FIG. 3 are provided as an example. In practice, the intraoperative imaging system 130 may include additional components, fewer components, different components, or differently arranged components than those shown in FIG. 3. Additionally, or alternatively, a set of components (e.g., one or more components) of the intraoperative imaging system 130 may perform one or more functions described as being performed by another set of components of the intraoperative imaging system 130.

Figure 4:
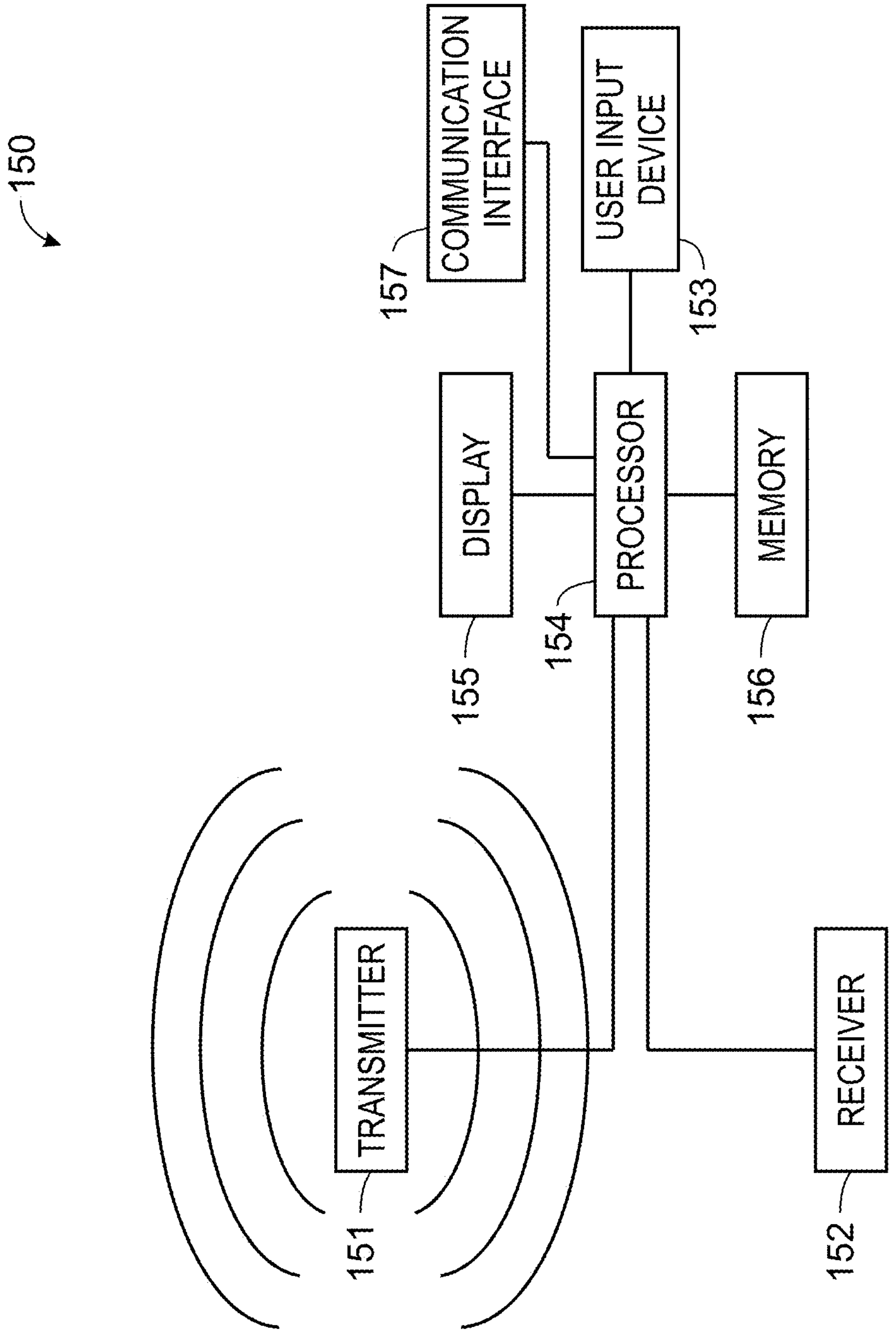
FIG. 4 is a diagram of example devices of a tracking system of FIG. 1.

FIG. 4 is a diagram of example devices of the tracking system 150. As shown in FIG. 4, the tracking system 150 may be an electromagnetic tracking system, and may include a transmitter 151, a receiver 152, a user input device 153, a processor 154, a display 155, a memory 156, and a communication interface 157.

The transmitter 151 may be configured to generate a magnetic field. The receiver 152 may be configured to output a signal in response to the magnetic field generated by the transmitter 151. The processor 154 may receive the output signal from the receiver 152, and acquire tracking data that identifies a position and/or an orientation of the receiver 152. The receiver 152 may be attached to, integrated with, provided in, etc., a tracked instrument. For example, according to an embodiment, the receiver 152 may be attached to the ultrasound probe 131 to track a position and/or an orientation of the ultrasound probe 131. Alternatively, the receiver 152 may be attached to a wand or other hand-held device to track a position and/or an orientation of the wand or the other hand-held device. Alternatively, the receiver 152 may be attached to an interventional device to track a position and/or an orientation of the interventional device. The interventional device may be a catheter, a needle, or the like.

The user input device 153 may be configured to receive a user input, and provide the user input to the processor 154. For example, the user input device 153 may be a touch screen display, a keyboard, a keypad, a mouse, a button, a switch, a microphone, or the like. Additionally, or alternatively, the user input device 153 may be configured to sense information. For example, the user input device 153 may sense information from an electro-magnetic positioning system, an inertial measurement system, an accelerometer, a gyroscope, an actuator, or the like.

The processor 154 may be configured to perform the operations as described herein. For example, the processor 154 may be a CPU, a GPU, an APU, a microprocessor, a microcontroller, a DSP, an FPGA, an ASIC, or the like. The processor 154 may be implemented in hardware, firmware, or a combination of hardware and software. The processor 154 may include one or more processors 154 configured to perform the operations described herein. For example, a single processor 154 may be configured to perform all of the operations described herein. Alternatively, multiple processors 154, collectively, may be configured to perform all of the operations described herein, and each of the multiple processors 154 may be configured to perform a subset of the operations descried herein. For example, a first processor 154 may perform a first subset of the operations described herein, a second processor 154 may be configured to perform a second subset of the operations described herein, etc.

The processor 154 may be configured to control the transmitter 151 to acquire ultrasound data. The processor 154 may be configured to control excitations of the transmitter 151 to generate a magnetic field. The processor 154 may acquire tracking data based on controlling the transmitter 151.

The display 155 may be configured to display information. For example, the display 155 may be a monitor, an LED display, a cathode ray tube, a projector display, a touchscreen, tablet computer, mobile phone, or the like. The display 155 may display the tracking data in real-time. For example, the display 155 may display the tracking data within one second, two seconds, five seconds, etc., of the tracking data being acquired.

The memory 156 may be configured to store information and/or instructions for use by the processor 154. The memory 156 may be a non-transitory computer-readable medium. For example, the memory 156 may be a RAM, a ROM, a flash memory, a magnetic memory, an optical memory, or the like. The memory 140 may be configured to store instructions that, when executed by the processor 155, cause the processor 155 to perform the operations described herein.

The communication interface 157 may be configured to enable the processor 154 to communicate with other systems, such as via a wired connection, a wireless connection, or a combination of wired and wireless connections. For example, the communication interface 157 may include an Ethernet interface, an optical interface, a coaxial interface, an infrared interface, an RF interface, a USB interface, a Wi-Fi interface, a cellular network interface, or the like.

The number and arrangement of the components of the tracking system 150 shown in FIG. 4 are provided as an example. In practice, the tracking system 150 may include additional components, fewer components, different components, or differently arranged components than those shown in FIG. 4. Additionally, or alternatively, a set of components (e.g., one or more components) of the tracking system 150 may perform one or more functions described as being performed by another set of components of the tracking system 150.

Although FIG. 4 depicts the tracking system 150 as being an electromagnetic tracking system, it should be understood that the embodiments herein are applicable to other types of tracking systems, such as optical tracking systems, acoustic tracking systems, ultrasound tracking systems, or the like.

Figure 5:
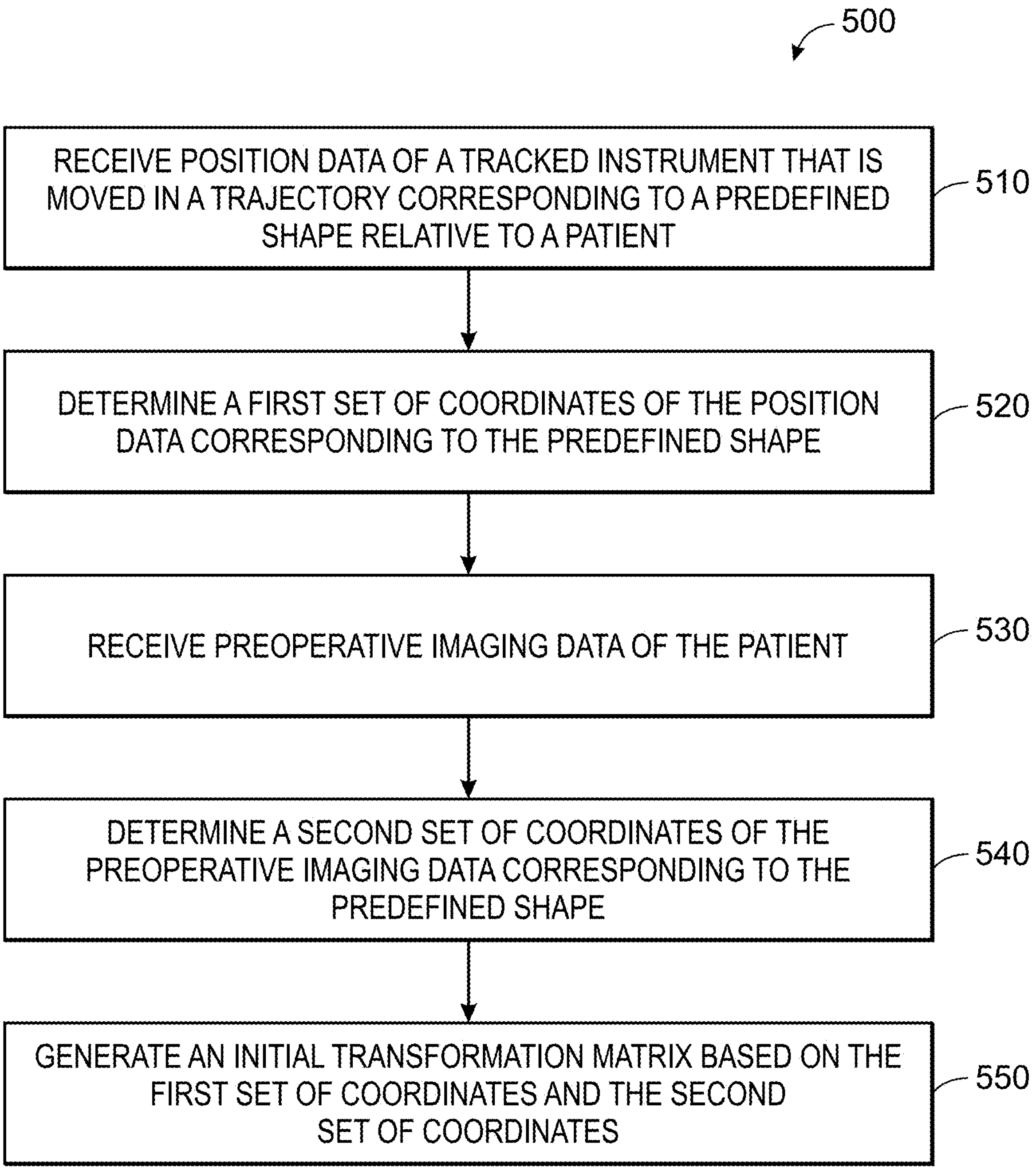
FIG. 5 is a flowchart of an example process for generating an initial transformation matrix for registering intraoperative imaging data with preoperative imaging data based on position data of a tracked instrument that is moved in a trajectory corresponding to a predefined shape relative to a patient.
Figure 6:
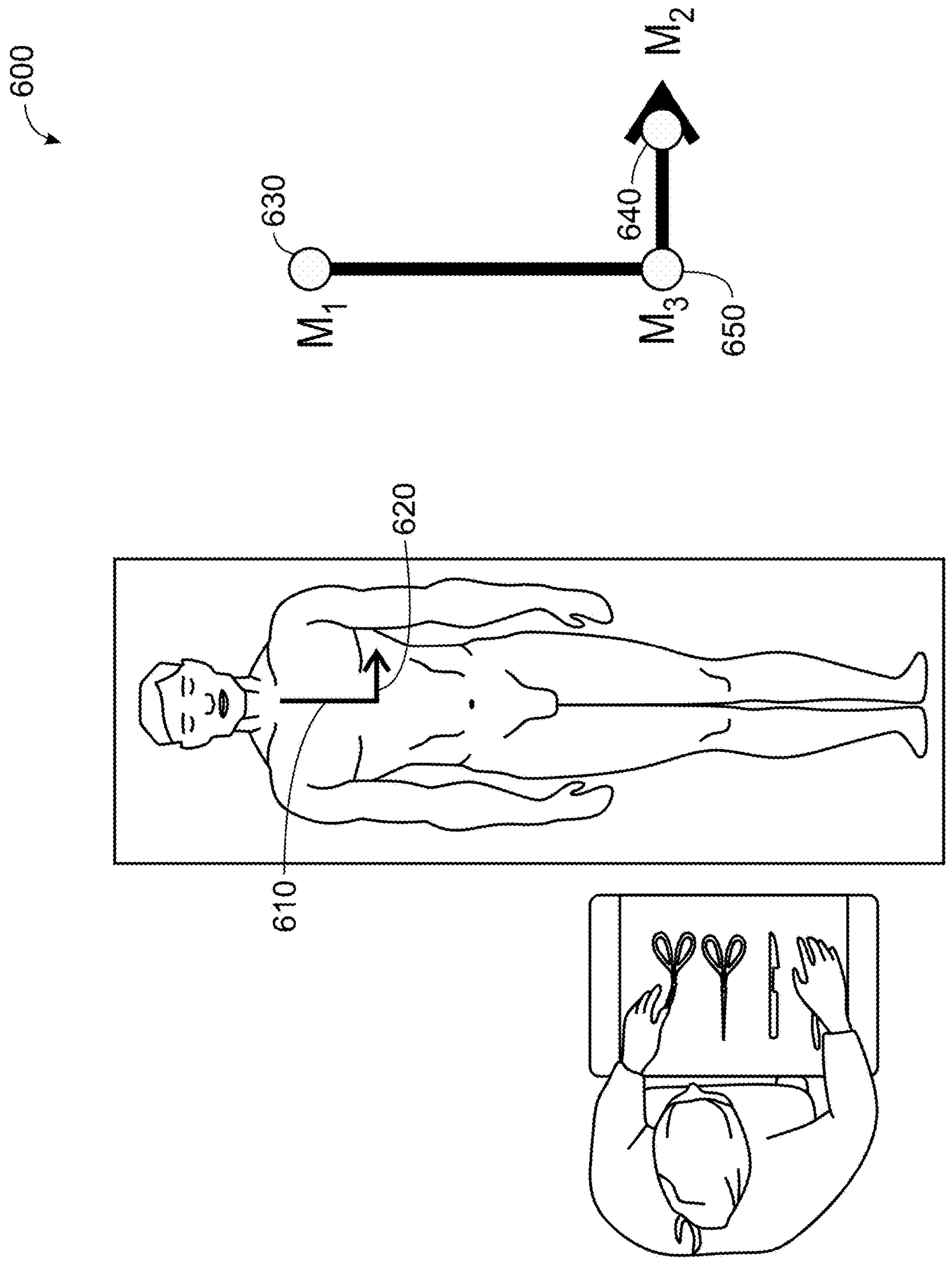
FIG. 6 is a diagram of an example movement of a tracked instrument that is moved in a trajectory corresponding to a predefined shape relative to a patient and example coordinates of position data of the tracked instrument.
Figure 7:
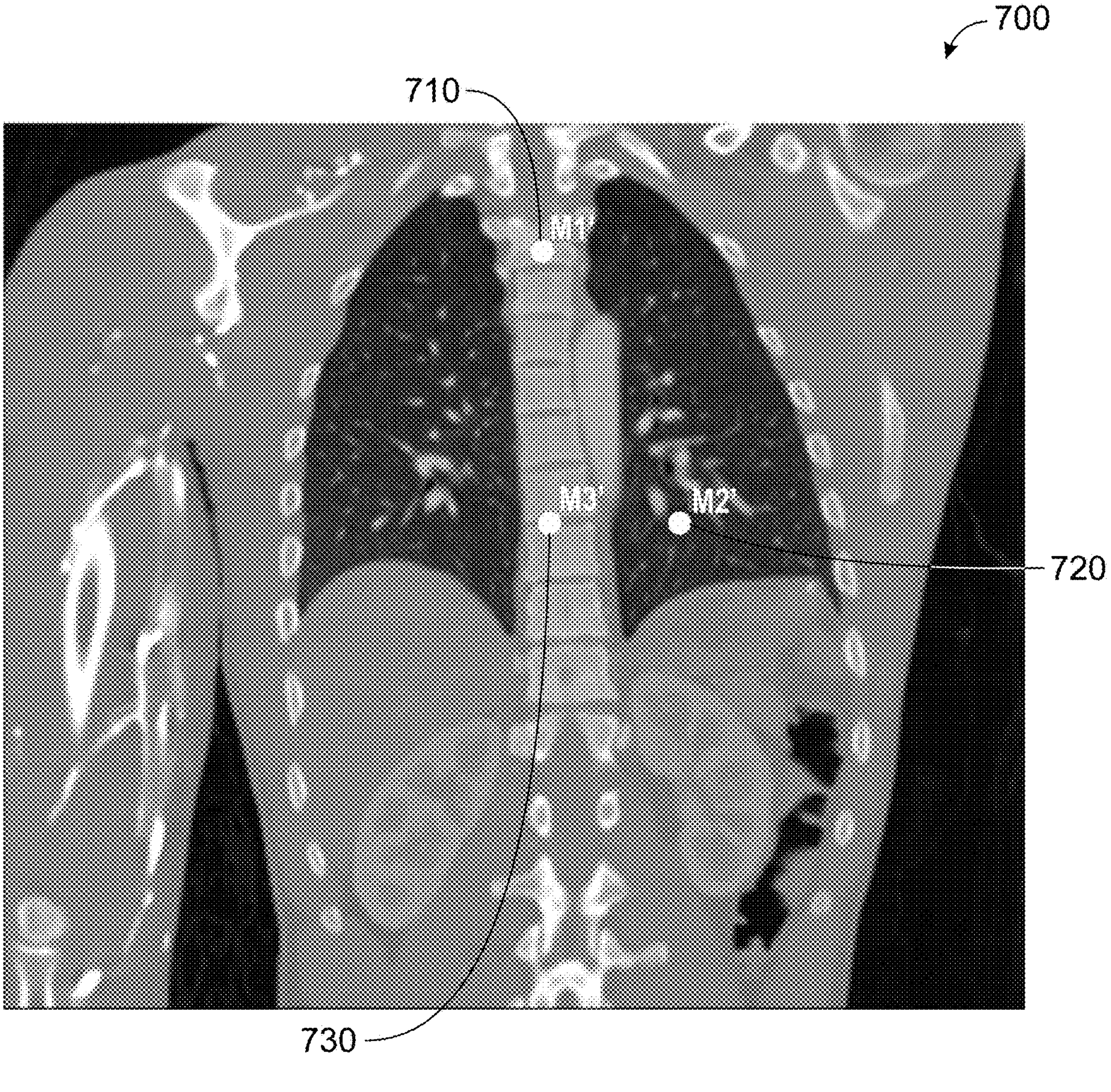
FIG. 7 is a diagram of an example set of coordinates of the preoperative imaging data corresponding to the predefined shape in FIG. 6.

FIG. 5 is a flowchart of an example process 500 for generating an initial transformation matrix for registering intraoperative imaging data with preoperative imaging data based on position data of a tracked instrument that is moved in a trajectory corresponding to a predefined shape relative to a patient. FIG. 6 is a diagram 600 of an example movement of a tracked instrument that is moved in a trajectory corresponding to a predefined shape relative to a patient and example coordinates of position data of the tracked instrument. FIG. 7 is a diagram 700 of an example set of coordinates of the preoperative imaging data corresponding to the predefined shape in FIG. 6.

As shown in FIG. 5, the process 500 may include receiving position data of a tracked instrument that is moved in a trajectory corresponding to a predefined shape relative to a patient (operation 510).

The tracked instrument may be any instrument that can be tracked. For example, the tracked instrument may be the ultrasound probe 131 of the intraoperative system 130. Additionally, or alternatively, the tracked instrument may be the ultrasound probe 131 including the receiver 152 of the tracking system 150. Alternatively, the tracked instrument may be a device including the receiver 152 of the tracking system 150. Alternatively, the tracked instrument may be a device that does not include the receiver of the tracking system 150. Alternatively, the tracked instrument may be a device such as a wand, a hand-held object, or the like.

The predefined shape may be any suitable shape. For example, the predefined shape may be an L-shape, a cross, a square, a rectangle, a line, an arc, or the like. According to an embodiment, the predefined shape may be a two-dimensional shape. For example, the predefined shape may extend along two axes. Alternatively, the predefined shape may be a three-dimensional shape. For example, the predefined shape may extend along three axes.

The tracked instrument may be moved in a trajectory corresponding to the predefined shape relative to a patient. For example, an operator may move the tracked instrument in a trajectory correspond to the predefined shape relative to a patient. The trajectory may be along the sagittal plane, the coronal plane, and/or the transverse plane of the patient. The trajectory may be superoinferior, inferosuperior, mediolateral, lateralmedial, anteroposterior, posteroanterior, or the like.

As an example, and as shown in FIG. 6, the predefined shape may be an L-shape. In this case, an operator may move the tracked instrument in a trajectory corresponding to the L-shape by making a superoinferior movement 610 and a lateral movement 620 with the tracked instrument.

The tracking system 150 may track the tracked instrument as the operator moves the tracked instrument in the trajectory relative to the patient. The tracking system 150 may transmit positon data of the tracked instrument to the registration system 110. The registration system 110 may receive the position data of a tracked instrument that is moved in a trajectory corresponding to a predefined shape relative to a patient from the tracking system 150.

According to an embodiment, the registration system 110 may display guidance information that guides an operator to move the tracked instrument in the trajectory corresponds to the predefined shape. For example, the registration system 110 may display a visual representation of the patient and a visual representation of the predefined shape relative to the patient. Additionally, or alternatively, the registration system 110 may display a live view of the tracked instrument, and may display guidance indicators that guide a direction of movement of the tracked instrument. According to an embodiment, the registration system 110 may determine, based on the positon data, that the predefined shape has been moved in the trajectory corresponding to the predefined shape relative to a patient. The registration system 110 may display information indicating that the operator has successfully moved the tracked instrument in the trajectory corresponding to the predefined shape relative to a patient.

As further shown in FIG. 5, the process 500 may include determining a first set of coordinates of the position data corresponding to the predefined shape (operation 520).

The first set of coordinates of the position data corresponding to the predefined shape may include one or more coordinates of the position data corresponding to the predefined shape. For example, the first set of coordinates may include coordinates of one or more points along the trajectory corresponding to the predefined shape relative to the patient. As an example, and as shown in FIG. 6, the first set of coordinates may include coordinates 630 of a point $M_1$ corresponding to the first position of the trajectory, coordinates 640 of a point $M_2$ corresponding to a last point in the trajectory, and coordinates 650 of a point $M_3$ corresponding to a point where the tracked instrument changes movement from the superoinferior direction to the lateral direction.

The first set of coordinates may be coordinates of an intraoperative coordinate system. The intraoperative coordinate system may be a coordinate system of the intraoperative imaging system 130 and/or the tracking system 150. For example, the intraoperative coordinate system may be a coordinate system for intraoperative images generated during a procedure.

According to an embodiment, the registration system 110 may fit a plane to a set of 3D points representing the predefined shape. The registration system 110 may project each point onto the plane. The registration system 110 may apply a piecewise linear function with two segments to the projected points. In this way, the registration system 110 may identify the primary breakpoint in the piecewise linear function, along with the starting and ending points of the function. The registration system 110 may determine the first set of coordinates using the points.

As further shown in FIG. 5, the process 500 may include receiving preoperative imaging data of the patient (operation 530), and determining a second set of coordinates of the preoperative imaging data corresponding to the predefined shape (operation 540).

The registration system 110 may receive preoperative imaging data of the patient from the preoperative imaging system 170, and determine a second set of coordinates of the preoperative imaging data corresponding to the predefined shape. The second set of coordinates may be coordinates of a preoperative coordinate system. The preoperative coordinate system may be a coordinate system of the preoperative imaging system 170 and/or a tracking system 150 associated with the preoperative imaging system 170.

The registration system 110 may determine the second set of coordinates using metadata of the preoperative imaging data. For example, the preoperative imaging data may be in the Digital Imaging and Communications in Medicine (DICOM) format. In this case, the registration system 110 may determine the second set of coordinates using the Patient Position (0018,5100) attribute that specifies the position of the patient relative to the imaging equipment space of the preoperative imaging system 170. Additionally, or alternatively, the registration system 110 may determine the second set of coordinates using the Image Orientation (0020,0037) attribute that specifies the orientation of the image frame rows and columns with respect to the patient. Additionally, or alternatively, the registration system 110 may determine the second set of coordinates using the Image Position (0020,0032) attribute which specifies the x, y, and z coordinates of the upper left hand corner of the preoperative image data. Additionally, or alternatively, the registration system 110 may determine the second set of coordinates using the Pixel Spacing (0028,0030) attribute that specifies the position and orientation of the image slices relative to a patient-based coordinate system. Additionally, or alternatively, the registration system 110 may use any other attribute to determine the second set of coordinates.

The registration system 110 may use any of the foregoing attributes to determine the second set of coordinates in the preoperative imaging data using the center of the preoperative imaging data as a reference point. Alternatively, the registration system 110 may use another portion of the preoperative imaging data as a reference point. The registration system 110 may determine the second set of coordinates based on the reference point. For example, the registration system 110 may determine a first point in the preoperative imaging data that is spaced a first predetermined distance from the reference point in a first direction, determine a second point in the preoperative imaging data that is spaced a second predetermined distance from the reference point in a second direction, determine a third point in the preoperative imaging data that is spaced a third predetermined distance from the reference point in a third direction, etc.

The second set of coordinates of the operative imaging data corresponding to the predefined shape may include one or more coordinates of the operative imaging data corresponding to the predefined shape. For example, the second set of coordinates may include coordinates of one or more points along the predefined shape relative. As an example, and as shown in FIG. 7, the second set of coordinates may include coordinates 710 of a point $M_1'$ corresponding to the first position of the predefined, coordinates 720 of a point $M_2'$ corresponding to a last point in the predefined shape, and coordinates 730 of a point $M_3'$ corresponding to a point where the predefined shape changes direction from the superoinferior direction to the lateral direction.

It should be understood that the predefined shape of the second set of coordinates of the preoperative imaging data corresponds to the predefined shape of the first set of coordinates of the position data. In other words, and referring to FIGS. 6 and 7, the predefined shape defined by the coordinates 630, 640, and 650 corresponds to the same predefined shape as defined by the coordinates 710, 720, and 730.

According to an embodiment, the registration system 110 may determine the predefined shape based on the first set of coordinates, and determine the second set of coordinates based on determining the predefined shape. Additionally, or alternatively, the registration system 110 may determine distances between the first set of coordinates, and determine the second set of coordinates based on the distances. For example, the registration system 110 may determine the second set of coordinates to include the same, or similar, distances as the distances between the first set of coordinates.

According to an embodiment, the registration system 110 may determine an orientation of the patient relative to the predefined shape made by the trajectory of the tracked instrument, and determine an orientation of the patient relative to the preoperative imaging data. The registration system 110 may determine the second set of coordinates based on the foregoing orientations. That is, the registration system 110 may determine the second set of coordinates to include a same orientation relative to the patient as the first set of coordinates.

As further shown in FIG. 5, the process 500 may include generating an initial transformation matrix based on the first set of coordinates and the second set of coordinates (operation 550).

The initial transformation matrix may transform the coordinates of the preoperative coordinate system to the coordinates of the intraoperative coordinate system. The registration system 110 may generate the initial transformation matrix using the first set of coordinates and the second set of coordinates. For example, the registration system 110 may generate the initial transformation matrix using a transformation matrix generation technique.

The initial transformation matrix may represent a rigid transformation that defines the alignment between two sets of corresponding 3D point data, derived from preoperative and intraoperative sources. The initial transformation matrix may describe how the preoperative imaging data should be rotated and translated to best match intraoperative imaging data.

The registration system 110 may identify corresponding points between the preoperative imaging data and the position data of the tracked instrument. For example, the registration system 110 may identify corresponding points between the second set of coordinates and the first set of coordinates. Subsequently, the registration system 110 may determine an alignment between the second set of coordinates and the first set of coordinates through the calculation of the initial transformation matrix. The registration system 110 may minimize, or reduce, the least squares errors between each point from the second set of coordinates and the first set of coordinates. For example, the registration system 110 may use the following equation to calculate the least squares errors between each point from the second set of coordinates and the first set of coordinates between the preoperative imaging data and the position data of the tracked instrument:

$$err = \sum_{i=1}^{n} \|RM_i' + t - M_i\|^2$$

In the above equation, err represents the least squares error, n is the number of coordinates in each set, M and M' are the first set of coordinates and the second set of coordinates, respectively, R is a 3×3 rotation matrix, and t is the translation vector. Sequentially, an iterative optimization algorithm is used to adjust the alignment parameters (translation, rotation) to minimize these errors. The initial transformation matrix may include both rotation and translation, and serves as the basis for aligning preoperative imaging data and intraoperative imaging data.

Figure 8:
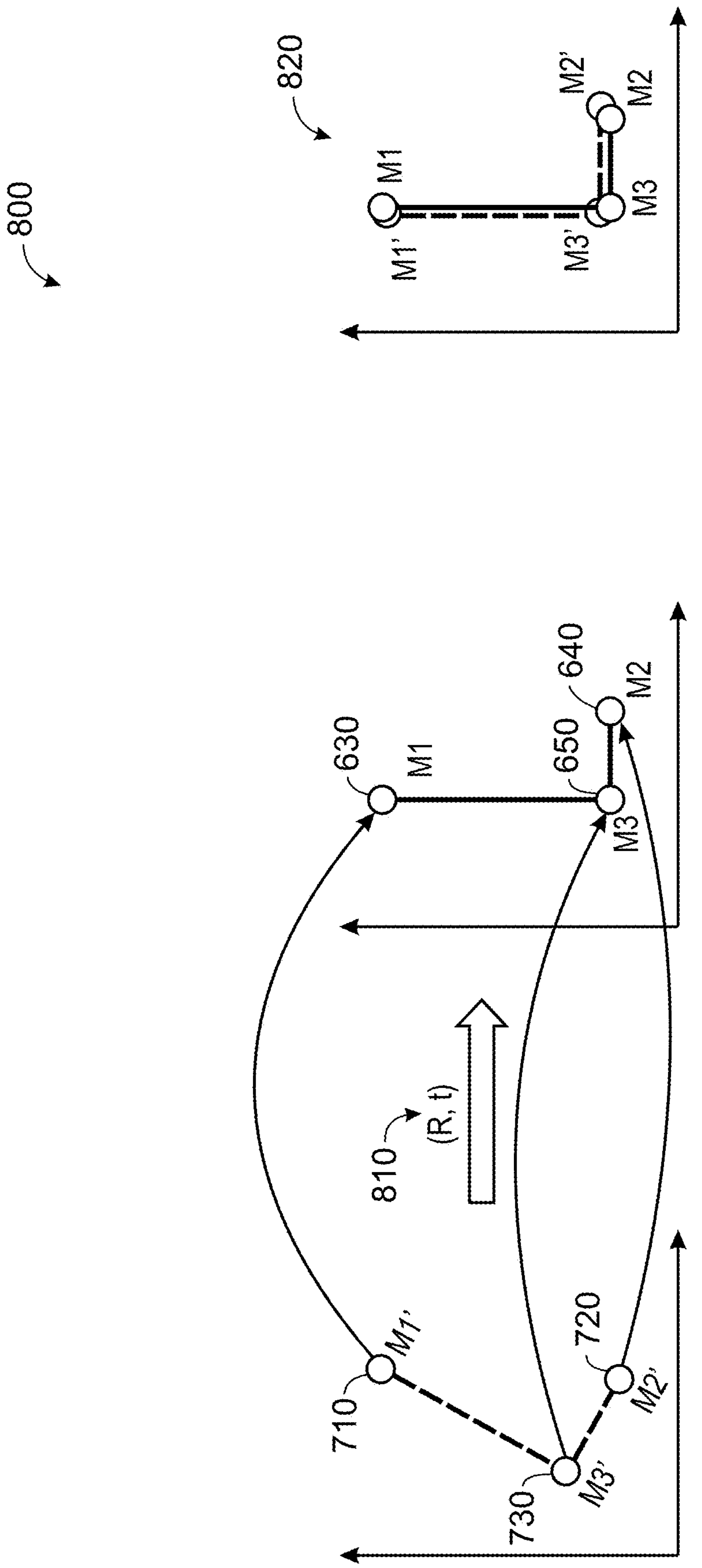
FIG. 8 is a diagram of a process of generating an initial transformation matrix based on the position data of the tracked instrument that is moved in the trajectory corresponding to the predefined shape relative to the patient in FIG. 6 and the example set of coordinates of the preoperative imaging data in FIG. 7 corresponding to the predefined shape in FIG. 6.

FIG. 8 is a diagram of a process 800 of generating an initial transformation matrix based on the position data of the tracked instrument that is moved in the trajectory corresponding to the predefined shape relative to the patient in FIG. 6 and the example set of coordinates of the preoperative imaging data in FIG. 7 corresponding to the predefined shape in FIG. 6. As shown in FIG. 8, the registration system 110 may use the initial transformation matrix 810 to transform the coordinates of the preoperative coordinate system to the coordinates of the intraoperative coordinate system. For example, the registration system 110 may transform the coordinates 710, 720, and 730 to the coordinates 630, 640, and 650, respectively. As shown by reference number 820, the coordinates 710, 720, and 730 may be more closely aligned to the coordinates 630, 640, and 650, respectively, after applying the transformation matrix 810.

Although the process 500 depicts a particular set of operations and a particular order of operations, it should be understood that the process 500 may include less operations, more operations, or differently arranged operations in other embodiments.

Figure 9:
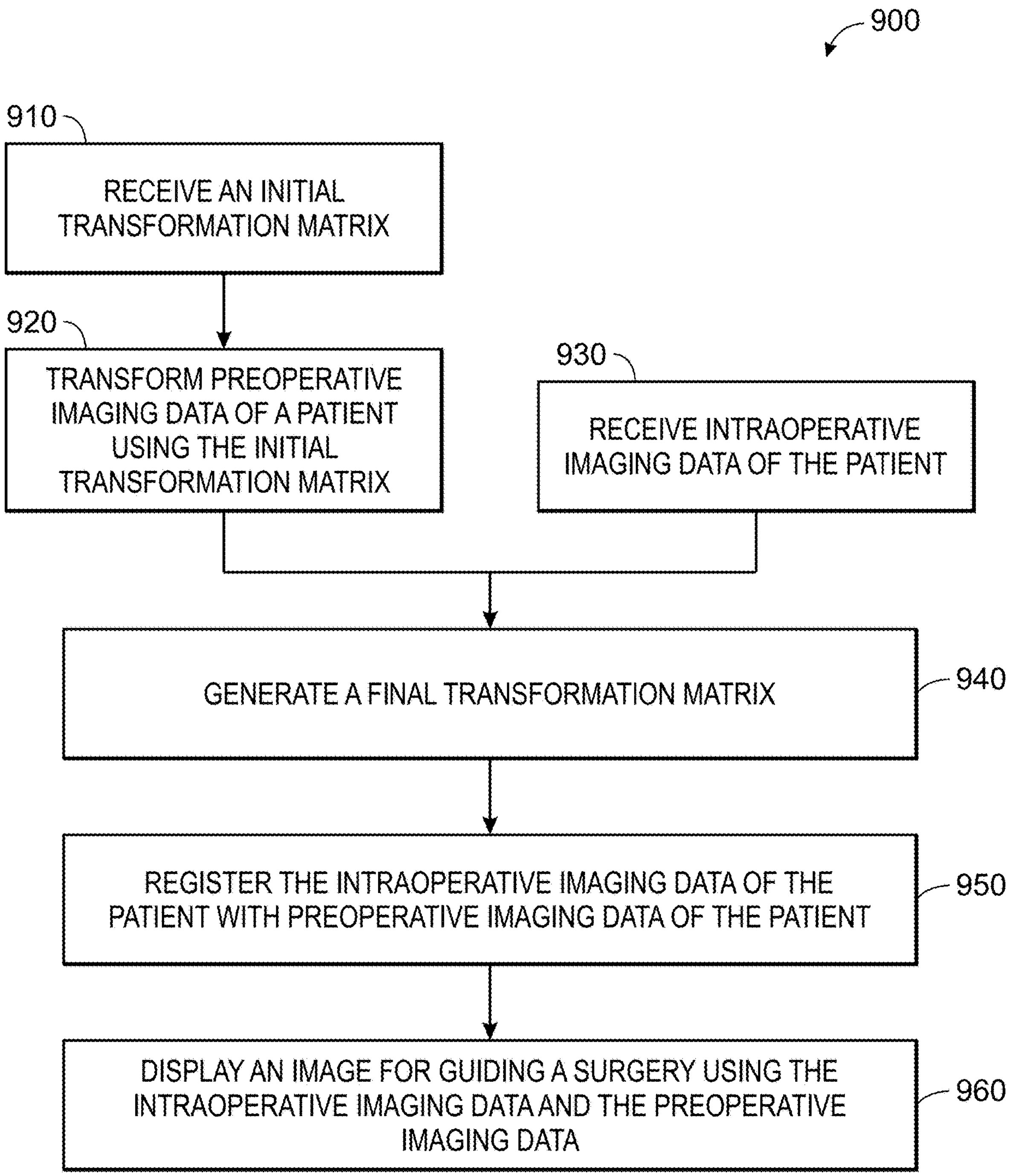
FIG. 9 is a flowchart of an example process for displaying an image for guiding a surgery using intraoperative imaging data that is registered with preoperative imaging data using an initial transformation matrix generated by the system of FIG. 1.

FIG. 9 is a flowchart of an example process 900 for displaying an image for guiding a surgery using intraoperative imaging data that is registered with preoperative imaging data using an initial transformation matrix generated by the system of FIG. 1.

As shown in FIG. 9, the process 900 may include receiving an initial transformation matrix (operation 910). The initial transformation matrix may be the initial transformation matrix generated in operation 550 of FIG. 5.

As further shown in FIG. 9, the process 900 may include transforming preoperative imaging data of a patient using the initial transformation matrix (operation 920). For example, the registration system 110 may transform the coordinates of the preoperative coordinate system to the coordinates of the intraoperative coordinate system.

As further shown in FIG. 9, the process 900 may include receiving intraoperative imaging data of the patient (operation 930). For example, the registration system 110 may receive intraoperative imaging data of the patient from the intraoperative imaging system 130.

As further shown in FIG. 9, the process 900 may include generating a final transformation matrix (operation 940). Based on the initial transformation matrix being generated, an operator begins scanning of the patient using the ultrasound probe 131 that is being tracked using the tracking system 150. Following the completion of the ultrasound data acquisition, the registration system 110 may three-dimensionally segment a same underlying anatomical structure within both the intraoperative imaging data and preoperative imaging data. The registration system 110 may transform the 3D segmented volume from the preoperative imaging data using the initial transformation matrix. This technique ensures that both of the preoperative coordinate system and the intraoperative coordinate system are close to each other, which simplifies and improves the final alignment process. According to an embodiment, the registration system 110 may use the Coherent Point Drift (CPD) algorithm for the final registration. The CPD algorithm is a probabilistic approach that aligns point sets, such as the segmented structures from the preoperative imaging data and the intraoperative imaging data. The CPD algorithm utilizes the segmented structures from both the intraoperative imaging data and the preoperative imaging data in the form of point clouds to determine the final registration. In this way, the CPD algorithm compares the spatial relationships between the points in both of the preoperative imaging data and the intraoperative imaging data to find the best, or improved, alignment.

In conclusion, the concept of utilizing an initial transformation is to align the coordinate systems within both the preoperative imaging data and the intraoperative imaging data, thereby enhancing robustness during registration with the final algorithm. Without employing this initial transformation, the disparities between the preoperative coordinate system and intraoperative coordinate system could be substantial, which could potentially cause the algorithm to fail. However, by ensuring that both the preoperative coordinate system and the intraoperative coordinate system are closely aligned through the calculation of the initial transformation matrix, the embodiments herein improve the resilience of the algorithm.

As further shown in FIG. 9, the process 900 may include registering the intraoperative imaging data of the patient with preoperative imaging data of the patient using the final transformation matrix (operation 950). For example, the registration system 110 may register the intraoperative imaging data with preoperative imaging data received from the preoperative imaging system 170 using the final transformation matrix.

As further shown in FIG. 9, the process 900 may include displaying an image for guiding a surgery using the intraoperative imaging data and the preoperative imaging data (operation 960). For example, the registration system 110 may display an image for guiding a surgery using the intraoperative imaging data and the preoperative imaging data. As an example, the image may be an image in which intraoperative imaging data is fused with preoperative imaging data. As another example, the image may be an image in which a virtual representation of an interventional device (e.g., a needle, a catheter, a stent, or the like) is displayed in relation to the intraoperative imaging data and/or the preoperative imaging data.

Figure 10:
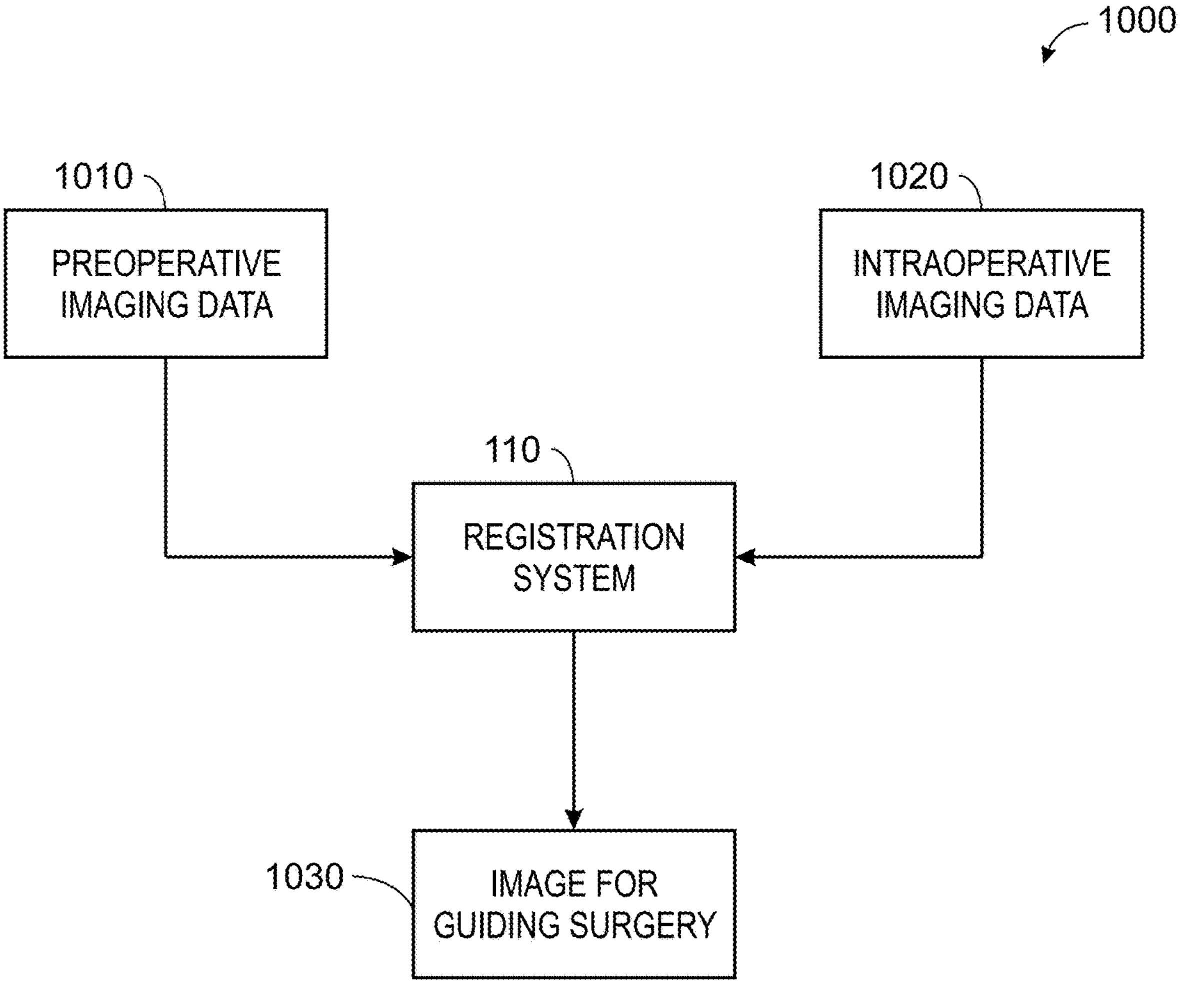
FIG. 10 is a diagram of an example process for displaying an image for guiding a surgery using intraoperative imaging data that is registered with preoperative imaging data using an initial transformation matrix and a final transformation matrix generated by the system of FIG. 1.

FIG. 10 is a diagram of an example process for displaying an image for guiding a surgery using intraoperative imaging data that is registered with preoperative imaging data using an initial transformation matrix and a final transformation matrix generated by the system of FIG. 1. For example, as shown, the registration system 110 may receive preoperative imaging data 1010 from the preoperative imaging system 170, and receive intraoperative imaging data 1020 from the intraoperative imaging system 130. The registration system 110 may generate and display an image 1030 for guiding surgery using the preoperative imaging data and the intraoperative imaging data. For example, the image 1030 may be an image including a fusion of intraoperative ultrasound data and preoperative CT data. However, it should be understood that any combination of data of different imaging modalities may be utilized to generate the image 1030.

Figure 11:
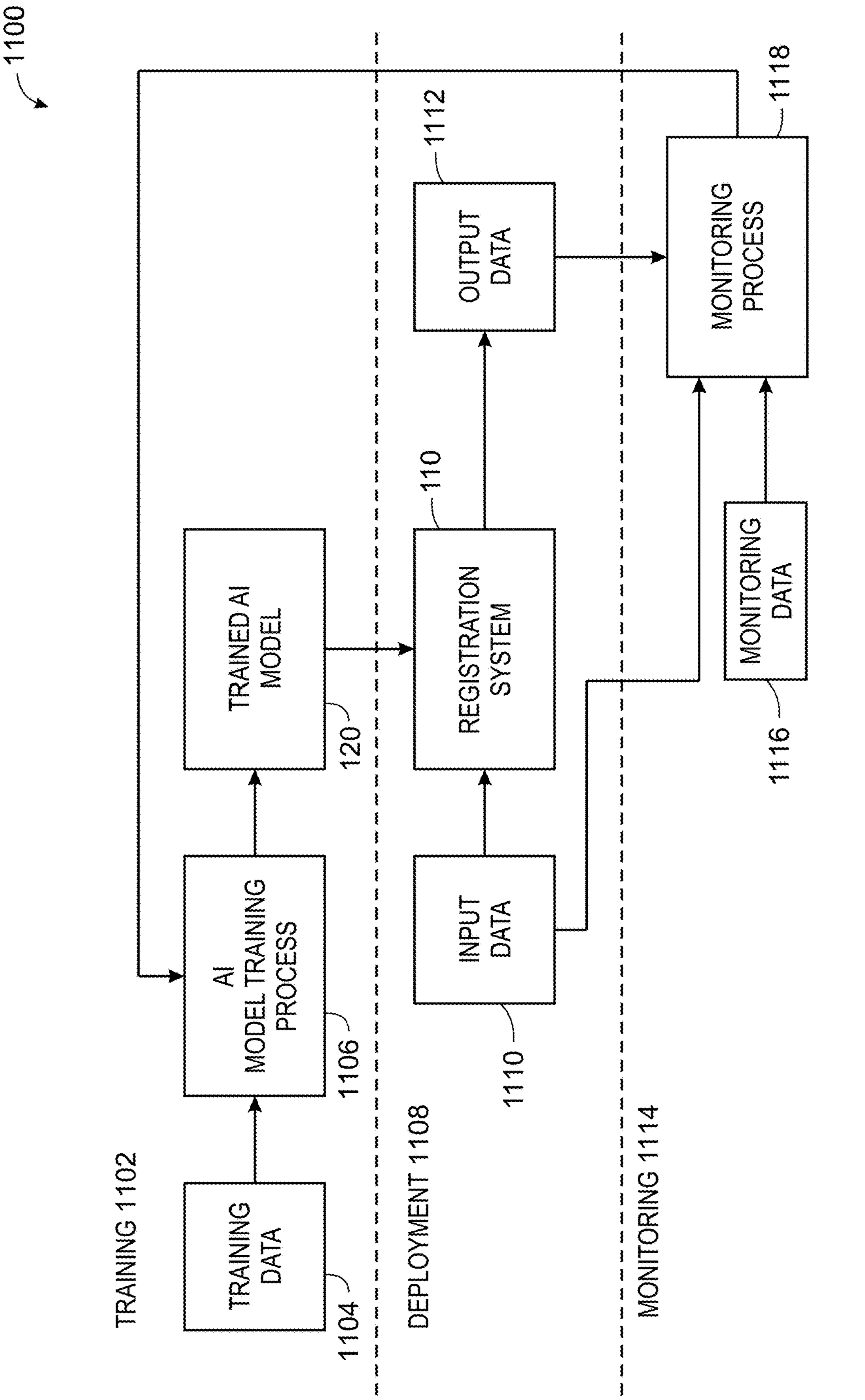
FIG. 11 is a diagram of training, deploying, and updating an artificial intelligence (AI) model to generate an initial transformation matrix.

FIG. 11 is a diagram of training, deploying, and updating an artificial intelligence (AI) model to generate an initial transformation matrix. The registration system 110 may generate, store, train, and/or use the AI model 120. According to an embodiment, the registration system 110 may include the AI model 120 and/or instructions associated with the AI model 120. For example, the registration system 110 may include instructions for generating the AI model 120, training the AI model 120, using the AI model 120, etc. According to an embodiment, a system or device other than the registration system 110 may be used to generate and/or train the AI model 120. For example, a system or device may include instructions for generating the AI model 120, and/or instructions for training the AI model 120. The system or device may provide a resulting trained AI model 120 to the registration system 110 for use.

As shown in FIG. 11, according to an embodiment, the process 1100 may include a training phase 1102, a deployment phase 1108, and a monitoring phase 1114. In the training phase 1102, at operation 1106, the process 1000 may include receiving and processing training data 1104 to generate a trained AI model 120. The training data 1104 may be generated, received, or otherwise obtained from internal and/or external resources.

Generally, the AI model 120 may include a set of variables (e.g., nodes, neurons, filters, or the like) that are tuned (e.g., weighted, biased, or the like) to different values via the application of the training data 1104. According to an embodiment, the training process at operation 1106 may employ supervised, unsupervised, semi-supervised, and/or reinforcement learning processes to train the AI model 120. According to an embodiment, a portion of the training data 1104 may be withheld during training and/or used to validate the trained AI model 120.

For supervised learning processes, the training data 1104 may include labels or scores that may facilitate the training process by providing a ground truth. For example, the labels or scores may indicate an output of the AI model 120. Training may proceed by feeding a training dataset including the training data 1104 into the AI model 120. The AI model 120 may have variables set at initialized values (e.g., at random, based on Gaussian noise, based on pre-trained values, or the like). The AI model 120 may generate an output based on the training dataset being input to the AI model 120. The output may be compared with the corresponding label or score (e.g., the ground truth) indicating the known output, which may then be back-propagated through the AI model 120 to adjust the values of the variables. This process may be repeated for a plurality of samples at least until a determined loss or error is below a predefined threshold. According to an embodiment, some of the training data 1104 may be withheld and used to further validate or test the trained AI model 120.

For unsupervised learning processes, the training data 1104 may not include pre-assigned labels or scores to aid the learning process. Instead, unsupervised learning processes may include clustering, classification, or the like, to identify naturally occurring patterns in the training data 1104. As an example, the training data may be clustered into groups based on identified similarities and/or patterns. K-means clustering or K-Nearest Neighbors may also be used, which may be supervised or unsupervised. Combinations of K-Nearest Neighbors and an unsupervised cluster technique may also be used. For semi-supervised learning, a combination of training data 1104 with pre-assigned labels or scores and training data 1104 without pre-assigned labels or scores may be used to train the AI model 120.

When reinforcement learning is employed, an agent (e.g., an algorithm) may be trained to make a decision from the training data 1104 through trial and error. For example, based on making a decision, the agent may then receive feedback (e.g., a positive reward if the prediction was above a predetermined threshold), adjust its next decision to maximize the reward, and repeat until a loss function is optimized.

After being trained, the trained AI model 120 may be stored and subsequently applied by the registration system 110 during the deployment phase 1108. For example, during the deployment phase 1108, the trained AI model 120 executed by the registration system 110 may receive input data 1110. During the deployment phase 1108, the trained AI model 120 may perform one or more operations as described in connection with FIGS. 5 and 8.

After being deployed, the trained AI model 120 may be monitored during the monitoring phase 1114. For example, during the monitoring phase 1114, the AI model 120 may generate monitoring data 1116 that is used to monitor the trained AI model 120. The monitoring data 1116 may include data that identifies an output as determined by an operator. During process 1118, the monitoring data 1116 may be analyzed along with the predicted output data 1112 and input data 1110 to determine an accuracy of the trained AI model 120. According to an embodiment, based on the analysis, the process 1100 may return to the training phase 1102, where at operation 1106 values of one or more variables of the model may be adjusted to improve the accuracy of the AI model 120.

The example process 1100 described above is provided merely as an example, and may include additional, fewer, different, or differently arranged aspects than depicted in FIG. 11.

FIG. 11 describes the training, deployment, and monitoring associated with a trained AI model 120. According to an embodiment, one or more other trained AI model 120*s* may be applied. Each of the trained AI model 120*s* may include similar training, deployment, and/or monitoring phases as described above for the trained AI model 120 in FIG. 11, however the particular types of training data, input data, output data, and monitoring data may be different.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

What is claimed is:

1. A method comprising:

receiving position data of a tracked instrument that is moved in a trajectory corresponding to a predefined shape relative to a patient;

determining a first set of coordinates of different points of the trajectory corresponding to the predefined shape based on the position data, wherein the first set of coordinates includes first coordinates of a first point of the trajectory, second coordinates of a last point in the trajectory, and third coordinates of a point in the trajectory where the tracked instrument changes from a superoinferior movement in a superoinferior direction relative to the patient to a lateral movement in a lateral direction relative to the patient;

receiving preoperative imaging data of the patient;

determining, using metadata of the preoperative imaging data and a reference point in the preoperative imaging data, a second set of coordinates corresponding to the predefined shape, wherein the second set of coordinates includes fourth coordinates of a first point in the preoperative imaging data that is spaced a first predetermined distance from the reference point in a first direction, fifth coordinates of a second point in the preoperative imaging data that is spaced a second predetermined distance from the reference point in a second direction, and sixth coordinates of a third point in the preoperative imaging data that is spaced a third predetermined distance from the reference point in a third direction;

identifying corresponding points between the first set of coordinates and the second set of coordinates;

determining an alignment between the first set of coordinates and the second set of coordinates using the corresponding points;

generating an initial transformation matrix based on the alignment between the first set of coordinates and the second set of coordinates;

receiving intraoperative imaging data and registering the intraoperative imaging data with the preoperative imaging data based on the initial transformation matrix;

generating an image for guiding a surgery using the intraoperative imaging data and the preoperative imaging data; and displaying the image for guiding the surgery.

2. The method of claim 1, further comprising:

generating a final transformation matrix based on the initial transformation matrix, wherein the registering the intraoperative imaging data with the preoperative imaging data comprises registering the intraoperative imaging data with the preoperative imaging data using the final transformation matrix.

3. The method of claim 1, further comprising:

determining distances between the first set of coordinates, wherein the determining the second set of coordinates of the preoperative imaging data comprises determining the second set of coordinates of the preoperative imaging data corresponding to the predefined shape based on the distances between the first set of coordinates.

4. The method of claim 1, wherein:

the initial transformation matrix transforms the first coordinates to the fourth coordinates, transforms the second coordinates to the fifth coordinates, and transforms the third coordinates to the sixth coordinates.

5. A device comprising:

a memory configured to store instructions; and one or more processors configured to execute the instructions to perform operations comprising:

receiving position data of a tracked instrument that is moved in a trajectory corresponding to a predefined shape relative to a patient;

determining a first set of coordinates of different points of the trajectory corresponding to the predefined shape based on the position data, wherein the first set of coordinates includes first coordinates of a first point of the trajectory, second coordinates of a last point in the trajectory, and third coordinates of a point in the trajectory where the tracked instrument changes from a superoinferior movement in a superoinferior direction relative to the patient to a lateral movement in a lateral direction relative to the patient;

receiving preoperative imaging data of the patient;

determining, using metadata of the preoperative imaging data and a reference point in the preoperative imaging data, a second set of coordinates corresponding to the predefined shape, wherein the second set of coordinates includes fourth coordinates of a first point of in the preoperative imaging data that is spaced a first predetermined distance from the reference point in a first direction, fifth coordinates of a second point in the preoperative imaging data that is spaced a second predetermined distance from the reference point in a second direction, and sixth coordinates of a third point in the preoperative imaging data that is spaced a third predetermined distance from the reference point in a third direction;

identifying corresponding points between the first set of coordinates and the second set of coordinates;

determining an alignment between the first set of coordinates and the second set of coordinates using the corresponding points;

generating an initial transformation matrix based on the alignment between the first set of coordinates and the second set of coordinates;

receiving intraoperative imaging data and registering the intraoperative imaging data with the preoperative imaging data based on the initial transformation matrix;

generating an image for guiding a surgery using the intraoperative imaging data and the preoperative imaging data; and displaying the image for guiding the surgery.

6. The device of claim 5, wherein the metadata includes at least one of a patient position attribute, an image orientation attribute, an image position attribute, and a pixel spacing attribute.

7. The device of claim 5, wherein the operations further comprise:

generating a final transformation matrix based on the initial transformation matrix, wherein the registering the intraoperative imaging data with the preoperative imaging data comprises registering the intraoperative imaging data with the preoperative imaging data using the final transformation matrix.

8. The device of claim 5, wherein the operations further comprise:

determining distances between the first set of coordinates, wherein the determining the second set of coordinates of the preoperative imaging data comprises determining the second set of coordinates of the preoperative imaging data corresponding to the predefined shape based on the distances between the first set of coordinates.

9. A non-transitory computer-readable medium storing instructions that, when executed by one or more processors, cause the one or more processors to perform operations comprising:

receiving position data of a tracked instrument that is moved in a trajectory corresponding to a predefined shape relative to a patient;

determining a first set of coordinates of different points of the trajectory corresponding to the predefined shape based on the position data, wherein the first set of coordinates includes first coordinates of a first point of the trajectory, second coordinates of a last point in the trajectory, and third coordinates of a point in the trajectory where the tracked instrument changes from a superoinferior movement in a superoinferior direction relative to the patient to a lateral movement in a lateral direction relative to the patient;

receiving preoperative imaging data of the patient;

determining, using metadata of the preoperative imaging data and a reference point in the preoperative imaging data, a second set of coordinates corresponding to the predefined shape, wherein the second set of coordinates includes fourth coordinates of a first point in the preoperative imaging data that is spaced a first predetermined distance from the reference point in a first direction, fifth coordinates of a second point in the preoperative imaging data that is spaced a second predetermined distance from the reference point in a second direction, and sixth coordinates of a third point in the preoperative imaging data that is spaced a third predetermined distance from the reference point in a third direction;

identifying corresponding points between the first set of coordinates and the second set of coordinates;

determining an alignment between the first set of coordinates and the second set of coordinates using the corresponding points;

generating an initial transformation matrix based on the alignment between the first set of coordinates and the second set of coordinates;

receiving intraoperative imaging data and registering the intraoperative imaging data with the preoperative imaging data based on the initial transformation matrix;

generating an image for guiding a surgery using the intraoperative imaging data and the preoperative imaging data; and displaying the image for guiding the surgery.

10. The non-transitory computer-readable medium of claim 9, wherein the metadata includes at least one of a patient position attribute, an image orientation attribute, an image position attribute, and a pixel spacing attribute.

11. The non-transitory computer-readable medium of claim 9, wherein the operations further comprise:

generating a final transformation matrix based on the initial transformation matrix, wherein the registering the intraoperative imaging data with the preoperative imaging data comprises registering the intraoperative imaging data with the preoperative imaging data using the final transformation matrix.

* * * * *